(12) United States Patent
Han et al.

(10) Patent No.: US 6,268,161 B1
(45) Date of Patent: Jul. 31, 2001

(54) BIOSENSOR

(75) Inventors: In Suk Han; You Han Bae; Jules J. Magda, all of Salt Lake City, UT (US); Seong Gi Baek, Woodbury, MN (US)

(73) Assignee: M-Biotech, Inc., Salt Lake City, UT (US)

( * ) Notice: Subject to any disclaimer, the term of this patent is extended or adjusted under 35 U.S.C. 154(b) by 0 days.

(21) Appl. No.: 09/308,392

(22) PCT Filed: Sep. 30, 1998

(86) PCT No.: PCT/US98/20750

§ 371 Date: May 11, 1999

§ 102(e) Date: May 11, 1999

(87) PCT Pub. No.: WO99/17095

PCT Pub. Date: Apr. 8, 1999

Related U.S. Application Data

(60) Provisional application No. 60/060,539, filed on Sep. 30, 1997, and provisional application No. 60/062,744, filed on Oct. 23, 1997.

(51) Int. Cl.[7] .............................. C12Q 1/54; C12M 1/34
(52) U.S. Cl. ........................ 435/14; 435/25; 435/287.1; 436/95; 604/891.1; 604/892.1
(58) Field of Search ..................... 435/14, 25, 287.1; 436/95, 148; 604/891.1, 892.1

(56) References Cited

U.S. PATENT DOCUMENTS

| | | | |
|---|---|---|---|
| 4,366,033 | 12/1982 | Richter et al. ................ | 204/1 T |
| 4,431,004 | 2/1984 | Bessman et al. ............. | 128/635 |
| 4,538,616 * | 9/1985 | Rogoff ........................... | 128/632 |
| 4,703,756 | 11/1987 | Gough et al. ................. | 123/635 |
| 4,919,141 | 4/1990 | Zier et al. ..................... | 128/635 |
| 4,953,552 | 9/1990 | DeMarzo ....................... | 128/635 |
| 4,981,779 | 1/1991 | Wagner ......................... | 435/288 |
| 5,005,403 * | 4/1991 | Steudle et al. ............... | 73/64.3 |
| 5,141,873 * | 8/1992 | Steudle et al. ............... | 436/148 |
| 5,305,745 | 4/1994 | Zacouto ........................ | 128/637 |
| 5,337,747 * | 8/1994 | Neftel ............................. | 128/635 |
| 5,372,133 | 12/1994 | Hogen Esch ................. | 128/631 |
| 5,431,160 | 7/1995 | Wilkins ......................... | 128/635 |
| 5,544,651 | 8/1996 | Wilk .............................. | 128/633 |
| 5,593,852 | 1/1997 | Heller et al. ................. | 435/14 |
| 5,624,537 | 4/1997 | Turner et al. ................ | 204/403 |
| 5,995,860 | 11/1999 | Sun et al. ..................... | 600/341 |
| 6,030,827 | 2/2000 | Davis et al. .................. | 435/287.1 |

OTHER PUBLICATIONS

Ito, Yoshihiro et al., An Insulin–Releasing System That Is Responsive To Glucose, J. of Controlled Release, 10 (1989) 195–203.

Lisa, Klumb et al., Design of insulin delivery devices based on glucose sensitive membranes, J. of Controlled Release, 18 (1992) 59–80.

(List continued on next page.)

*Primary Examiner*—David A. Redding
(74) *Attorney, Agent, or Firm*—Morriss, Bateman, O'Bryant & Compagni

(57) ABSTRACT

A biosensor (10) has a pH-sensitive polymeric hydrogel (30) in a rigid and preferably biocompatible enclosure (20). The hydrogel (30) includes an immobilized oxidoreductase enzyme such as glucose oxidase. The oxidoreductase enzyme catalyzes a chemical reaction consuming an organic molecule and producing a byproduct. The hydrogel (30) changes its osmotic pressure in proportion to the concentration of a byproduct. By measuring the change in osmotic pressure with a pressure transducer (40), the biosensor (10) is able to accurately measure the concentration of the organic molecule without the problem of interference encountered by prior art biosensors. A battery (64) powered telemeter (60) operably engaged to the pressure transducer (40) sends a radio data signal to a receiver (66) operably attached to a computer (62).

20 Claims, 6 Drawing Sheets

OTHER PUBLICATIONS

Shuji Sato et al., Self–regulating insulin delivery systems, J. of Controlled Release, 1 (1984) 67–77.

Seo Young et al., Self–regulating insulin delivery systems, J. of Controlled Release, 1 (1984) 57–66.

Marian F. McCurley et al., Swelling of a Polymer Membrane for Use in a Glucose Biosensor, © 1992 American Chemical Society.

Stuart J. Updike et al., Improved Long–Term Performance In Vitro and In Vivo, ASAIO Journal 1994.

Christopher D. Batich, Swelling Behavior of pH–Sensitive Copolymers Based on Styrene and 4–(or–2) Vinylpridine, Macromolecules 1993, 26, 4675–4680.

Dean R. Harrison et al., A Diode–Quad Bridge Circuit for Use with Capacitance Transducers, Rev. Sci. Instrum., vol. 44, No. 10, Oct. 1973.

Ronald A. Siegel et al., pH–Dependent Equilibrium Swelling Properties of Hydrophobic Polyelectrolyte Copolymer Gels, Macromolecules 1988, 21 3254–3259.

Kazuhiko Ishihara et al., Glucose–Responsive Insulin Release from Polymer Capsule, J. of Polymer Science: Polymer Letters Edition, vol. 24, 413–417 (1986).

Martin Pradny et al., Martin Pradny et al., Hydrogels for site–specific oral delivery, Makromol. Chem. 191, 1887–1897 (1990).

Kazuhiko Ishihara et al., Control of Insulin Permeation through a Polymer Membarane with Responsive Function for Glucose, Makromol. Chem., Rapid Commun. 4, 327–331 (1983).

Kazuhiko Ishihara et al., Glucose Induced Permeation Control of Insulin through a Complex Membrane consisting of Immobilized Glucose Oxidase and a Poly(amine), Polymer Journal, vol. 16, No. 8, pp 625–631 (1994).

Robert Puers, Capacitive sensors:when and how to use them, Sensor and Actuators a. 37–38 (1993) 93–105.

M.Y. Arica et al., Glucose oxidase sandwiched between pHEMA layers: a continuous flow reactor application, Biomaterial 1993, vol. 14 No. 11.

Gerard Reach et al., Can Continuous Glucose Monitoring Be Used for the Treatment of Diabetes, Analytical Chemistry, vol. 64, No. 6, Mar. 15, 1992.

J.S. Tan et al., Surface modification of nanoparticles by PEO/PPO block copolymers to minimize interactions with blood components and prolong blood circulation in rats, Bio–materials 1993, vol. 14 No. 11.

Harry R. Allcock et al., Synthesis and characterization of pH–sensitive poly–(organophosphazene) hydrogels, Biomaterials 1996, vol. 17 No. 23.

Y. Arica et al., Immobilization of glucose oxidase in poly (2–hydroxyethyl methacrylate) membranes, Department of Biological Sciences, Bio–material Research Laboratory, Ankara 06531, Turkey.

Lisa Brannon–Peppas et al., Dynamic and equilibrium swelling behavior of pH–sensitive hydrogels containing 2–hydroxyethyl metharcrylate, biomaterials 1990, vol. 11 Nov.

Beck,Sg. Pressure Measuring System, PhD Thesis University of Utah 1991.

* cited by examiner

BIOSENSOR

This application for a utility patent follows a previously filed provisional patent Ser. No. 60/060,539 (titled Glucose Sensor Based On Glucose Sensitive Hydrogels And Pressure Sensing Technologies) having a filing date of Sep. 30, 1997 and provisional patent Ser. No. 60/062,744 (titled Method For Biosensor) having a filing date of Oct. 23, 1997.

This invention was made with government support under R43DK55959 (grant/contract no.) awarded by the National Institute of Health. The Government has certain rights in this invention.

BACKGROUND OF THE INVENTION

1. Filed of the Invention

This invention generally relates to a biosensor for measuring the concentration of organic molecules in a solution, and more particularly to an implantable glucose monitoring device using a glucose sensitive hydrogel and a pressure transducer, the device being proportionally responsive to increases in glucose levels in the blood when it is implanted.

2. Description of Related Art

Diabetes is one of the major diseases in the United States. In 1995, there were approximately sixteen million Americans suffering from diabetes, including those undiagnosed. It is estimated that 650,000 new cases are diagnosed each year. Diabetes was the seventh leading cause of the death listed on U.S. death certificates in 1993, according to the National Center for Health Statistics. There are two major types of diabetes: type I diabetes (10% of diabetes cases in the United States), and type II diabetes (90 % of diabetes cases in the United States). Type I diabetes is caused by an insulin deficiency due to the destruction of the pancreatic beta cells, and requires daily treatment with insulin to sustain life. Type II diabetes is caused by target organ insulin resistance resulting in a decreased responsiveness to both endogenous and exogenous insulin, and is usually managed by diet and exercise but may require treatment with insulin or other medication. Most people diagnosed with type II diabetes are over 40 years old.

Diabetes disturbs the body's ability to control tightly the level of blood glucose which is the most important and primary fuel of the body. Insulin is a critical hormone needed to keep glucose concentrations within very narrow physiological limits in normal people though high levels of carbohydrates may be consumed. Not only is insulin secreted by the beta cells of the pancreas, but also its levels are rapidly regulated by glucose concentrations in the blood. Insulin allows the passage of glucose into the targets cells which contain receptors for uptake of glucose. Diabetic patients with an elevated glucose level in the blood, hyperglycemia, have either an insulin deficiency or a decreased responsiveness to insulin.

Hyperglycemia adversely affects other physiological processes. For example, hyperglycemia causes severe water loss and dehydration. Water loss can be so severe that it decreases blood pressure, and the reduced blood pressure may lead to brain damage. As discussed in National Diabetes Data Group, National Institutes of Health, National Institute of Diabetes and Digestive and Kidney Diseases, "Diabetes In America," 2nd edition, NIH Publication No. pp. 95–1468, (1995), patients of diabetes are often subject to destructive alterations of other physiological processes, causing blindness, heart attack, stroke, periodontal disease, neuropathy, nephropathy, and atherosclerosis resulting from hyperglycemia. Tissue damage can be so extensive that amputations are required to save the patient. Also, there is always the danger in diabetics of hypoglycemia due to diet, with an insulin injection required to bring the blood glucose level back up to normal. Hypoglycemic episodes can occur without the diabetic patient being aware of it. It is required to maintain a balance between insulin injection and glucose consumption to prevent hypoglycemia. However, the condition is not fatal if proper care is taken.

In treating diabetic patients, the aim is to tightly regulate the plasma glucose level within the normal physiological range (80–120 mg/dL), so that diabetic adverse effects can be avoided. Self-monitoring of blood glucose levels using dry chemical strips with a single drop of blood is considered a major advance in diabetes management. This in vitro method of monitoring of blood glucose has two main disadvantages. The first is that sampling of blood is associated with the risk of infection, nerve and tissue damage, and discomfort to patients. The second disadvantage is the practical limitation in self-monitoring which arises because the sampling frequency is not great enough for tight control of blood glucose levels close to normal ranges over a 24-hr period. Thus, as an aid to diabetes therapy, continuous monitoring of blood glucose concentrations in vivo has long been recognized as a major objective as a future tool in the fight against diabetes.

During the past decade, intense effort has been directed toward the development of glucose monitoring biosensors as an aid to diabetes therapy. Development of an implantable glucose sensor that is specific to glucose and sensitive enough to precisely measure glucose levels in vivo would be a significant advance in the treatment of diabetes. Such ability to more closely control blood glucose levels would help prevent of complications commonly brought on by diabetes. Such a sensor would also greatly facilitate glucose level data collection, glycemia research, and development of an insulin delivery system responsive to glucose levels in diabetic patients.

Several new implantable techniques have been developed for glucose analysis in clinical practice based on electrochemical principles and employing enzymes such as glucose oxidase (GOD) for glucose recognition. Potentially implantable glucose biosensors based on electrochemical transducers are the most highly developed, and this class of sensors can be further subdivided into potentiometric sensors, conductometric sensors, and amperometric sensors. The local pH change due to production of gluconic acid in the above reaction can be measured with a pH-selective electrode or an ion selective field effect transistor (ISFET), which is the basis of the potentiometric method. Similarly, in the conductometric method, changes in the electrical resistance due to the progress of the above reaction are measured. At present, neither the potentiometric method nor the conductometric method appears to be suitable for in vivo glucose monitoring due to: (a) interference by species other than glucose in the physiological environment; (b) low sensitivity and logarithmic dependence of the signal on the glucose concentration. A linear dependence of the signal on glucose concentration is highly desirable because of the need for repeated recalibrations over time for implanted glucose sensors. However, non-linear calibration curves can be handled reasonably well using microprocessors.

The most advanced glucose sensors for in vivo monitoring are electrochemical sensors using the amperometric technique, possibly because they do offer the possibility for a linear calibration curve. In the amperometric method, an electrode is used which produces a current proportional to the diffusional flux of hydrogen peroxide ($H_2O_2$) to the electrode surface, or, alternatively, proportional to the diffisional flux of oxygen ($O_2$) to the electrode surface. The electrode is surrounded by a membrane layer containing immobilized GOD. The glucose reaction catalyzed by GOD given earlier produces hydrogen peroxide and consumes oxygen. An increase in the surrounding glucose concentration should increase the diffusional flux of glucose into the membrane and increase the reaction rate within the membrane. The increase in reaction rate in turn should increase the local hydrogen peroxide concentration and decrease the local oxygen concentration within the membrane. This should lead to an increase in the current detected by a hydrogen peroxide-based electrode sensor, or a decrease in current as detected by an oxygen-based electrode sensor. The latter approach, based on detecting the oxygen flux, also requires a second oxygen-based electrode sensor located in a hydrogel without the GOD enzyme. This second electrode is used as a reference. Amperometric sensors must overcome several hurdles before they will ever be useful for commercial in vivo monitoring. Current glucose sensor designs appear unlikely to solve these difficult problems in the near future. The first hurdle arises from electrochemical interference. The analyte (whether hydrogen peroxide or oxygen) must be the only species present which produces a current at the electrode. Hence for both oxygen-based and hydrogen peroxide-based glucose sensors, an inner membrane must be used which is permeable to the analyte but impermeable to endogenous interferents. This is a difficult goal to achieve due to the heavily "contaminated" nature of blood. Secondly, for the hydrogen peroxide-based sensor, mass transfer coefficients for diffusion of glucose and oxygen into the membrane containing GOD must not change with time due to an adsorbed layer. Thirdly, for both types of amperometric sensors, GOD must not deactivate with time. In clinical studies of the hydrogen peroxide-based sensor, a decay in sensitivity over the implant period was observed, a phenomenon which could not be explained by blockage of the sensor surface by protein. One possible explanation for the loss of sensitivity is hydrogen peroxide mediated GOD deactivation. For the oxygen-based sensor, this can be avoided by co-immobilizing catalase with GOD, because catalase consumes hydrogen peroxide. Fourthly, a shortage of oxygen relative to glucose can place an upper limit on the biosensor's ability to measure glucose levels. This problem is called the "oxygen deficit".

In addition to the biosensors described above, several glucose release mechanisms have been developed to release insulin directly into a diabetic's bloodstream in response to high glucose levels. One approach is to use a hydrogel having immobilized GOD, the hydrogel swelling with increases in glucose concentration using essentially the same physical phenomenon which will be employed in the glucose biosensor, described below. The amount of swelling in the insulin delivery devices was used to control insulin permeability through a hydrogel membrane. For example, as discussed shortly, the proposed biosensor infers changes in glucose concentration from changes in osmotic pressure. The osmotic pressure of a hydrogel in a confined space should have a much stronger dependence on the degree of swelling (and, indirectly, on the glucose concentration) than the rate of permeation through the gel.

The prior art teaches glucose biosensors that utilize the GOD enzyme in a hydrogel, but the prior art relies on direct electrode measurement of the resulting chemical reactions. The prior art does not teach the measurement of the glucose-induced swelling of the hydrogel as a method of measuring glucose concentrations. The prior art specifically does not teach the use of a transducer to measure hydrogel swelling in response to increases in glucose levels in the blood, the use of the transducer providing a measurement tool that avoids the problems encountered by the prior art, described above. The present invention fulfills these needs and provides further related advantages as described in the following summary.

SUMMARY OF THE INVENTION

The present invention teaches certain benefits in construction and use which give rise to the objectives described below.

The present invention provides a biosensor for measuring the concentration of an organic molecule in a solution. The biosensor includes a pH-sensitive polymeric hydrogel in a rigid and preferably biocompatible enclosure. The hydrogel includes an immobilized oxidoreductase enzyme. The oxidoreductase enzyme catalyzes a chemical reaction consuming the organic molecule and producing a byproduct. The hydrogel changes its osmotic pressure in proportion to the concentration of a byproduct. By measuring the change in osmotic pressure with a means for measuring, preferably a pressure transducer, the biosensor is able to accurately measure the concentration of the organic molecule without the problem of interference encountered by prior art biosensors. A means for reporting the concentration of the organic molecule, preferably a battery powered telemeter, is operably engaged with the means for measuring, and sends a radio data signal to a receiver operably attached to a computer.

A primary objective of the present invention is to provide a biosensor having advantages not taught by the prior art.

Another objective is to provide a biosensor that is extremely sensitive to the concentration of a single organic molecule, and also relatively free from interference, even when operating in complex media such as human blood.

A further objective is to provide a biosensor that relies on change in pH to measure an organic molecule such as glucose, pH being a much more controlled parameter than parameters measured directly by electrodes. This is especially critical in implantable biosensors because living creatures closely regulate body pH, thereby removing a potential source of interference.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE INVENTION

Figure 1:
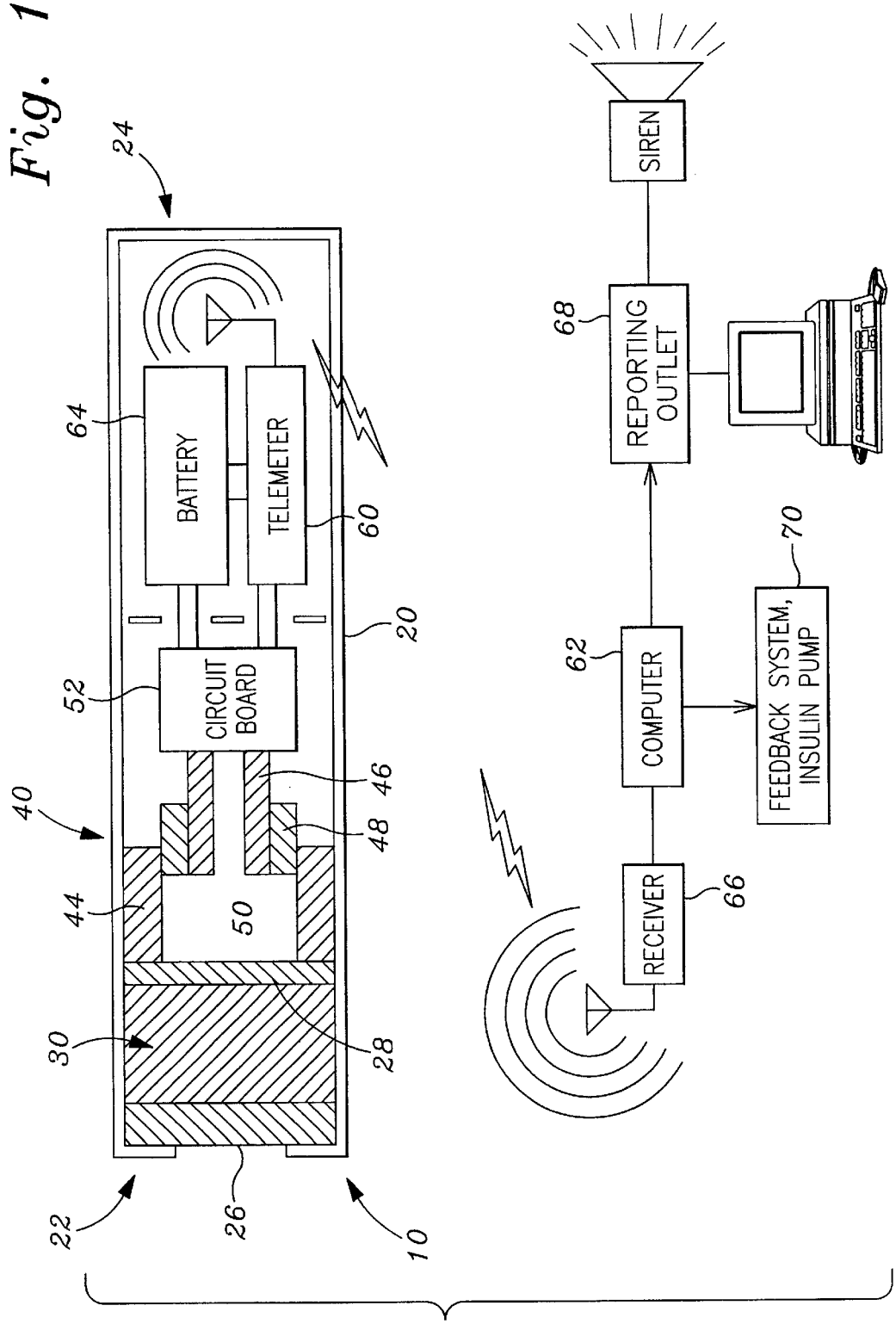
FIG. 1 is a side elevational sectional view of the preferred embodiment of the present invention, showing a biosensor that can be implanted under a diabetic's skin.

The above described drawing figures illustrate the invention, a biosensor 10 for measuring the concentration of an organic molecule in a solution. In its broadest description, the biosensor uses a special polymeric hydrogel that changes its osmotic pressure in proportion to the concentration of a byproduct; an oxidoreductase enzyme immobilized in the hydrogel 30, the oxidoreductase enzyme catalyzing a chemical reaction consuming the organic molecule and producing the byproduct, thereby causing the hydrogel to change its osmotic pressure; a means for measuring 40 the osmotic pressure of the hydrogel 30; and a means for reporting 60 the concentration of the organic molecule based on the measured osmotic pressure of the hydrogel 30. In its preferred embodiment, the biosensor includes a rigid, biocompatible enclosure 20 having semipermeable membrane 26 covering an open end 22 a flexible diaphragm 28 between the semipermeable membrane 26 and the closed end 24, and a polymeric hydrogel enclosed therebetween, the hydrogel including moieties that cause the hydrogel 30 to change its osmotic pressure in proportion to the pH of the hydrogel 30. The enclosure 20 is designed to be implanted directly into the human body for monitoring blood glucose levels of diabetics. In this embodiment, the biosensor 10 uses GOD as the oxidoreductase enzyme immobilized in a hydrogel 30. The means for measuring 40 the osmotic pressure of the hydrogel is preferably a pressure transducer 40 operably associated with the flexible diaphragm 28. The means for reporting 60 glucose levels is preferably a battery 64 operated telemeter 60 that sends a radio data signal to a receiver operably attached to a computer 62. Alternative embodiments of this biosensor can easily be adapted by those skilled in the art. The biosensor can be adapted to measure almost any organic molecule by replacing GOD with an appropriate oxidoreductase enzyme. Rather than use of a telemeter 60, direct electrical connection to a computer 62 can be used when the biosensor does not have to be implanted into a human body. While the pressure transducer 40 is currently the preferred tool for measuring changes in the osmotic pressure of the hydrogel 30, those skilled in the art can devise alternative means of measuring and reporting changes in the osmotic pressure of the hydrogel 30. One alternative method is to use a piezoelectric sensor on place of the pressure transducer 40.

The Enclosure, Semipermeable Membrane, and Diaphragm

As best shown in FIG. 1, the structure of the biosensor 10 is provided by an enclosure 20, preferably a cylindrical enclosure 20 having an open end and a closed end. The open end is sealed with a semipermeable membrane 26. A flexible diaphragm 28 is mounted between the semipermeable membrane 26 and the closed end. The hydrogel 30, described below, is enclosed between the semipermeable membrane 26 and the diaphragm 28. The enclosure 20 is preferably constructed of a rigid, impermeable, and biocompatible material such as stainless steel; and the enclosure 20 is preferably conjugated with heparin to prevent blood clotting, and polyethylene glycol (PEG) to decrease the body's immune response against the enclosure 20. The enclosure 20 is preferably cylindrical in shape to facilitate implantation, the cylinder being approximately 12 mm long and having a diameter of approximately 3 mm. If the enclosure 20 will not be implanted, any rigid and impermeable material such as fiber, plastic or metal can be used.

The semipermeable membrane 26 is permeable to the passage of glucose, oxygen, and gluconic acid; however, it is impermeable to the passage of blood clots, cells, proteins, and the hydrogel 30. The semipermeable membrane 26 is preferably made of a material rigid enough to sustain the pressure of a swollen glucose sensitive hydrogel 30. If the biosensor is to be implanted into the human body, the semipermeable membrane 26 is preferably an inert, nontoxic material. A suitable semipermeable material can be selected from, but is not limited to, the following groups of polymers: cellulose acetate, methyl cellulose, polyvinyl alcohol, and polyurethane. The semipermeable materials are also preferably conjugated with heparin and polyethlyene glycol (PEG) to decrease immunogenic response, blood clotting and cell attachment on the surface. Examples of such enclosures and semipermeable membranes are discussed in Heller, U.S. Pat. No. 5,593,852, Wilkins, U.S. Pat. No. 5,431,160, Hogen Esch, U.S. Pat. No. 5,372,133, Zier, U.S. Pat. No. 4,919,141, and Gough, U.S. Pat. No. 4,703,756, all hereby incorporated in full by reference.

The diaphragm 28 is preferably be a flexible but conductive material useful for use with a transducer 40. Such diaphragms are known in the art. The preferred diaphragm 28 is mode of an alloy sold under the trademarks KOVAR™ or INVAR 36™ by Hamilton Technology, Inc., of Lancaster, Pa. The diaphragm 28 is preferably approximately 12.5 um to achieve optimum spot welding and sensitivity. Such a diaphragm is described in Baek S G. Ph.D. Thesis, University of Utah, (1992). The diaphragm 28 is preferably seal welded to the enclosure 20 between the semipermeable membrane 26 and the closed end 24 of the enclosure 20. The hydrogel fills the chamber within the enclosure 20 between the semipermeable membrane 26 and the diaphragm 28. The means for measuring 40 and the means for reporting 60 described below, are located the chamber within the enclosure 20 between the diaphragm 28 and the closed end 24 of the enclosure 20.

pH-Sensitive Hydrogels

Hydrogels are defined as polymeric materials which swell in water and other solvents, absorbing the fluid within the polymer network without dissolving. Hydrophilic hydrogels have a large amount of water content at equilibrium and good biocompatibility. pH-sensitive hydrogels have been the most widely studied of the hydrophilic hydrogels. The pH-sensitive hydrogels are cross-linked to form a stabilized gel with several types of crosslinking forces such as covalent bonds, hydrogen bonds, or hydrophobic interactions. Acidic hydrogels by definition will be ionized and hence swollen at high pH, and uncharged and un-swollen at low pH. Swelling behavior of a basic hydrogel has the opposite dependence on pH. The pH sensitivity is caused by pendant acidic and basic groups such as carboxylic acid, sulfonic acid, primary amine, and quatemary ammonium salts. Carboxylic acid groups for example are charged at high pH and uncharged at low pH, whereas the reverse is true for primary amine groups and quaternary ammonium salts. The transition pH for a given pendant group is determined by the pKa value for that pendant group. Hence by choosing pendant groups with the appropriate pKa values, a hydrophilic hydrogel can be constructed which can be ionized reversibly in response to any level of pH stimuli leading to changes in properties of a gel. In the instant invention, the preferred range of pKa lies between 11 and 3.

The most important property of pH-sensitive hydrogel is its the degree of swelling in response to pH. The preferred pH-sensitive hydrogels are derived from a number of polymeric compounds such as: poly(aklyl acrylate), poly (acrylmethacrylate), poly(2-hydroxyethyl methacrylate) (HEMA), poly(2-hydroxypropylmethacrylate) (HPMA), poly(acrylamide), poly(N-vinyl pyrrolidone), poly(vinyl alcohol) (PVA), polyethylene oxide (PEO), poly (etherurethane), and polyelectrolyte. The monomers used to synthesize the homopolymers just listed can also be used in various combinations to form copolymers. pH-sensitive hydrogels formed from these polymers reversibly contract and dilate upon addition of acid and alkaline alternately. It has been shown that the response to a pH change can be very fast and reversible after abrupt changes in pH for poly (methyl methacrylate-co-N,N-dimethylaminoethyl methacrylate) hydrogels. Specific combinations of these compounds can be devised by those skilled in the art to meet the requirements of a specific type of biosensor Factors Influencing The Degree Of Swelling Of pH-Sensitive Hydrogels The equilibrium degrees of swelling and the conformation changes of pH-sensitive hydrogels are influenced by several factors such as the charge of the ionic monomer, pKa of the ionizable group, concentrations of ionizable pendant group in the network, pH, ionic strength, the dielectric constant of the medium, crosslinking density, hydrophilicity and hydrophobicity of polymer backbone. These factors are discussed in Helle Bronsdted and Jindrich Kopecek, pH-Sensitive Hydrogel; Characteristics And Potential In Drug Delivery in Properties, Preparation, and Application (Edited by Ronald S. Harland and Robert K. Prudhornme), 1992.

The charge of the ionic monomer influences the conformational changes of pH-sensitive hydrogels. An acidic hydrogel will be uncharged at low pH, but it will be ionized at the high pH. Thus, the equilibrium degree of swelling will increase when pH is enhanced in a hydrogel containing acidic pendant groups. Swelling of a basic hydrogel has the opposite dependence on pH. The hydrogels which are based on methacrylic acid, sulfoxyethyl methacrylate, HEMA, and HPMA, and have been generally used to obtain acid, basic, and ampholytic gels. Swelling as a function of the type of ionic groups has been studied. The pKa value of pendant ionizable groups in the gel is shown to influence the pH-swelling curve. A decrease in the pKa value of a basic ionizable group shifts the curve toward lower pH. It has been demonstrated that the swelling response is most sensitive to pH at a pH value close to the pKa value of the ionizable group of the hydrogel. The concentration of ionizable monomers in the hydrogel is significant to the swelling and pH-sensitivity of the gel. This effect depends on the relative hydrophilicity of the ionizable monomer compared to the neutral co-monomer. The hydrophobicity and hydrophilicity of the backbone of the pH-sensitive polymer affects swelling. It has been shown that increasing hydrophobicity of the polymer backbone decreases the pH-sensitivity of the copolymer poly(n-alkyl methacrylate-co-N,N-dimethylaminoethyl methacrylate) and copolymer styrene and 4-vinyl pyridine (VP). Buffer composition and ionic strength affect the swelling of the pH-sensitive hydrogels. Counterions shield charges on the polymeric backbones. The concentration of ions inside and outside of the gel will be equal as well as osmotic pressure inside the gel will decrease when the concentration of ions outside the gel increases. A buffer containing multivalent ion is able to neutralize several charges inside the gel. Cross-linking density is important for pH-sensitive swelling. The equilibrium degree of swelling will be restricted by an increased cross-linking density. This effect is more pronounced if the gel is ionized by a pH change. The network properties of the hydrogels are mainly influenced by the synthesis variables, particularly chemical composition and cross-linking density. Thus, chemical composition and synthesis conditions are important when attempting to control the equilibrium swelling properties of the gels to be studied in this phase of the research.

The preferred glucose biosensor will use a pH-sensitive hydrogel which includes copolymers synthesized from various types of methacrylate derived monomers by free radical solution polymerization. These copolymers are tough, flexible polymers rather than soft gels; they are highly biocompatible; and they are inert and nondegradable in vivo, a preferred trait for biosensors that are to be implanted into the human body. For example, the swelling of gels which are copolymers of N,N-diethyl-aminoethyl methacrylate (DEAMA) and 2-hydroxypropylmethylacrylate (HPMA) increases with decreasing pH of the medium. This has been shown in Ishihara K. Kobayashi M. Ishimaru N. Shinohara I. Poly J. 16:625–631, (1984), hereby incorporated by reference. By contrast, the water content of the HEMA homopolymer was independent of the pH of the medium. Thus the change in water content with pH of the HPMA copolymer hydrogel resulted from the introduction of the DEAMA moiety. The DEAMA moiety is considered to be protonated when the pH of the medium decreases, which increases the hydrophilicity of the DEAMA moiety and the hydrogel. The water content of DEAMA and HPMA copolymer hydrogel is reversible with respect to pH changes. Thin and tough polymers including HPMA and HEMA have been prepared which retaining at least equal and in some cases higher GOD activity than other polymer and porous support immobilization systems.

The Oxidoreductase Enzyme

The polymeric hydrogel 30 of this invention includes a supply of immobilized oxidoreductase enzyme. The oxidoreductase enzyme catalyzes a chemical reaction in the presence of oxygen and the organic molecule. The chemical reaction consumes the organic molecule and produces the byproduct. As described below, the byproduct causes the hydrogel to change its osmotic pressure and osmotic pressure in proportion to the concentration of the byproduct. In its preferred embodiment, the hydrogel 30 further includes immobilized catalase to prevent $H_2O_2$ from degrading the oxidoreductase enzyme. Other potential additions include an electron acceptor mediator such as ferrocene. An electron acceptor mediator is known as an "oxygen substitute" because it functions in the role of oxygen in the below-described reaction. Including ferrocene serves to resolve the "oxygen defecit." However, such mediator molecules are often toxic, so if they are used they must not diffuse out of the hydrogel 30. Special crosslinking in the hydrogel can help prevent ferrocene diffusion.

pH-Sensitive Hydrogels Containing GOD

As discussed above, the general combination of a polymeric hydrogel 30 and an oxidoreductase enzyme is what is important to this aspect of the invention. The specific parameters of the polymeric hydrogel and the specific oxidoreductase enzyme, and therefore the byproduct produced, will depend on what organic molecule is being measured. In the preferred biosensor 10, testing for glucose, GOD is used as the oxidoreductase enzyme. Immobilization of GOD by matrix entrapment in the gel is simpler and more reproducible than other techniques, such as surface immobilization technique, and hence is the preferred method of immobilizing GOD in the glucose biosensor 10. Glucose reacts with GOD to product gluconic acid as the relevant byproduct, according to the following formula:

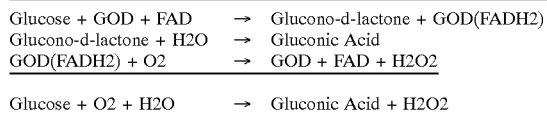

To function in the invention, the hydrogel is preferably pH-sensitive co-polymeric gel that contains immobilized GOD acts as a sensor of glucose, because according to the reaction given earlier, the glucose is converted to gluconic acid which lowers the pH. The catalyst (GOD) for this reaction is very highly specific for glucose resulting in production of gluconic acid and hydrogen peroxide in the presence of glucose and oxygen. The rate of gluconic acid and hydrogen peroxide formation is proportional to the glucose concentration in the hydrogel 30 at the reaction location. Large swelling changes are possible, as shown in Ishihara K. Kobayashi M. Ishimaru N. Shinohara I. Poly J. 16:625–631, (1984), herein incorporated by reference in full. These results were obtained using a gel based on the copolymer of HPMA and DEAMA containing GOD. Changes in glucose concentrations resulted in changes in pH due to the GOD catalyzed production of gluconic acid within the gel. The gluconic acid protonated the amine groups of the gel producing a charged hydrogel 30 network. Electrostatic repulsive forces between the amino groups increased the hydrogel 30 swelling by the large amounts. To function in the invention, the hydrogel 30 preferably includes pendant groups such as tertiary amines. The hydrogel 30 most preferably includes nicotinamide moieties.

As disclosed in Quinn C P, Pathak C P. Heller A, Hubbell J A. Biomaterial 16:389–396, (1995), it is possible to use a hydrogel 30 with immobilized GOD in a glucose biosensor for which changes in glucose were inferred by measuring the rate of hydrogen peroxide production (another product of the glucose / GOD reaction described above). However, since hydrogen peroxide tends to degrade the GOD enzyme, as discussed in Wilkins, U.S. Pat. No. 5,431,160, hereby incorporated by reference, it is not preferred to rely on a system that measures hydrogen peroxide production. Rather than measure the hydrogen peroxide, it is preferred to include catalase to eliminate the hydrogen peroxide as quickly as possible, and instead measure the increase in gluconic acid.

Some examples of appropriate systems with GOD immobilization are hydrogels 30 based on a collagen-based copolymer, an acrylic-based copolymer, a HPMA-based copolymer, and a HEMA-based copolymer. These hydrogels 30 are sufficiently permeable to glucose and oxygen, but not to high molecular weight proteins. The relative permeability of glucose and oxygen in the polymeric hydrogel 30 can be controlled by changing the ratio of monomer compositions such as crosslinkers in the copolymer. The copolymers used to make the pH-sensitive hygrogels 30 contain a certain number of amine groups and/or nicotinamide moieties which are involved in the swelling process. These pH-sensitive hydrogels containing GOD swell in the presence of glucose and greatly increase their water content. In some hydrogels, the gluconic acid and the hydrogen peroxide produced by the GOD enzymatic reaction are both involved in swelling the hydrogel. The gluconic acid protonates the amine groups on the copolymer resulting in production of a charged hydrogel 30 network. The charged amine enhances electrostatic repulsive forces and hydrophilicity in the hydrogel promoting an increase in the hydrogel 30 swelling. Furthermore, the redox copolymer containing the nicotinamide moiety is changed from reduced form (hydrophobic) to oxidized form (hydrophilic) by hydrogen peroxide, which also helps swell the hydrogel. The water content of pH-sensitive hydrogels containing pendant tertiary amino groups or nicotinamide groups is drastically increased by the enzymatic conversion of glucose which produces gluconic acid and lowers the local pH value. See Klumb L A, Horbett T A. J. Control. Release 18:59–80, (1992); Ishihara K, Kobayashi M, Shionohara I. Makromol. Chem. Rapid Commun. 4:327–331, (1983); Sato S, Jeong S Y, McRea J C, Kim S W. J. Control. Release 1:67–77, (1984); and Ito Y, Casolaro M, Kono K, Imanishi Y. J. Control. Release 10:195–203, (1989), hereby incorporated by reference. The swelling rates of glucose responsive pH-sensitive hydrogels are dependent on the glucose concentration in the hydrogel.

As shown in the above formula, oxygen is required to complete the GOD catalysis of glucose to gluconic acid. Due to the low concentration of oxygen in comparison to the concentration of glucose, however, oxygen is often a limiting factor in this reaction. Low oxygen levels often place an upper limit on glucose measurement. This problem has been referred to as the "oxygen deficit." To resolve this "oxygen deficit" problem, the semipermeable membrane 26 can be modified to allow oxygen to diffuse across the semipermeable membrane 26 at a greater rate that the organic molecule. Such an approach has been shown to eliminate the oxygen deficit problem with hydrogen peroxide-based glucose sensors, provided that the oxygen tension near the sensor is greater than pO2 8 mm Hg. Fortunately, the oxygen tension near a sensor implanted subcutaneously is expected to be in the range pO2 20–25 mm Hg. Many investigators have developed glucose restriction membranes to decrease influx of glucose into probes compared to the oxygen influx. The preferred glucose restriction membrane 26 is the memrbane developed by Markwell Medical Institute, of Racine, Wi. Alternatively, the semipermeable membrane 26 can be modified with a partial phospholipic coating or diamond-like carbon coating. This can be used to make the semipermeable membrane 26 more restrictive to glucose diffusion than to oxygen diffusion. In addition to modifications of the semipermeable membrane 26, other elements can be added to the biosensor to resolve the oxygen deficiency. The hydrogel 30 preferably includes crosslinking that allows oxygen to diffuse into the hydrogel 30 at a greater rate that the organic molecule. An oxygen reservoir can be used to alleviate oxygen deficit. Other approaches for counting the oxygen deficit include adding an oxygen substitute such as ferrocene to the hydrogel 30 30. Although ferrocene is toxic, special crosslinking in the hydrogel 30 can keep the ferrocene from diffusing out of the biosensor 10.

The above-description of hydrogels, useful for measuring GOD catalyzed reactions, are discussed in Heller, U.S. Pat. No. 5,593,852, Wilkins, U.S. Pat. No. 5,431,160, Hogen Esch, U.S. Pat. No. 5,372,133, Zier, U.S. Pat. No. 4,919,141, and Gough, U.S. Pat. No. 4,703,756, all hereby incorporated in full by reference.

Means for measuring—Pressure Transducer

The biosensor includes a means for measuring 40 the osmotic pressure of the hydrogel 30. This element is critical. While prior art biosensors rely on direct measurement of the GOD catalyzed chemical reaction with an electrode, measurement of the increase in osmotic pressure and chemically induced swelling has never been used in the prior art. A biosensor that relies on change in pH to measure an organic molecule avoids an important source of outside interference. pH is a much more controlled parameter than parameters measured directly by electrodes. This is especially critical in an implantable biosensor 10 because living creatures closely regulate body pH, thereby removing a potential source of interference.

Figure 4:
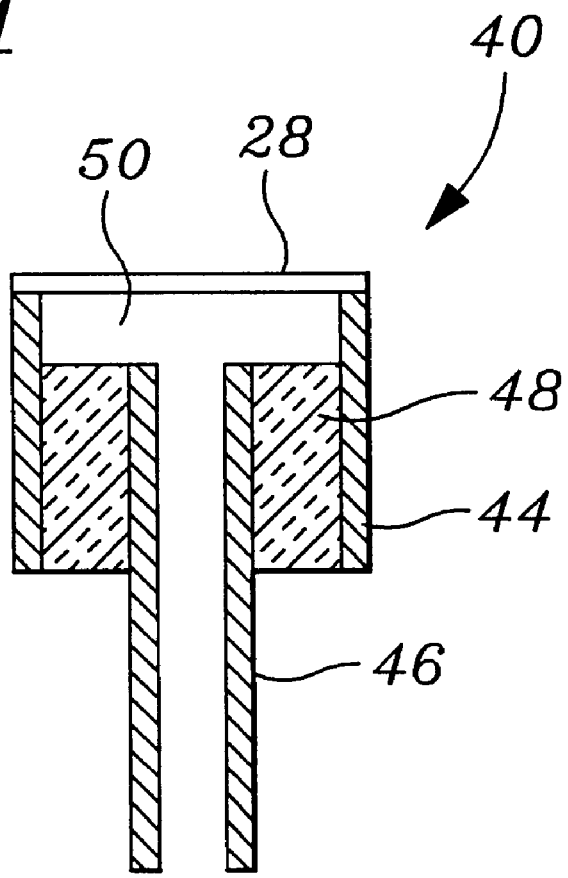
FIG. 4 is side elevational sectional view of the transducer.
Figure 5:
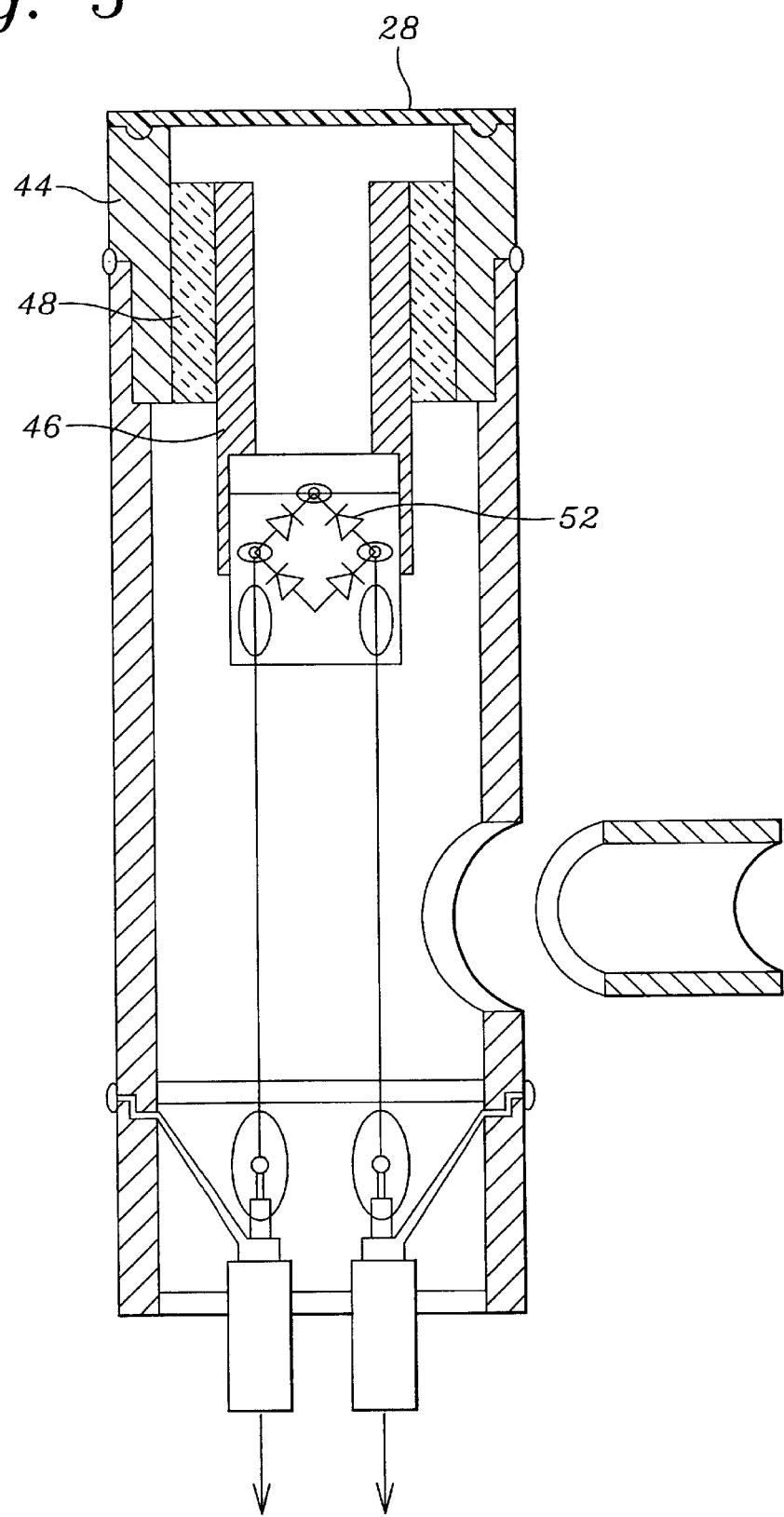
FIG. 5 is side elevational sectional view of the transducer including the preferred circuit board having a diode quad bridge circuit.
Figure 6:
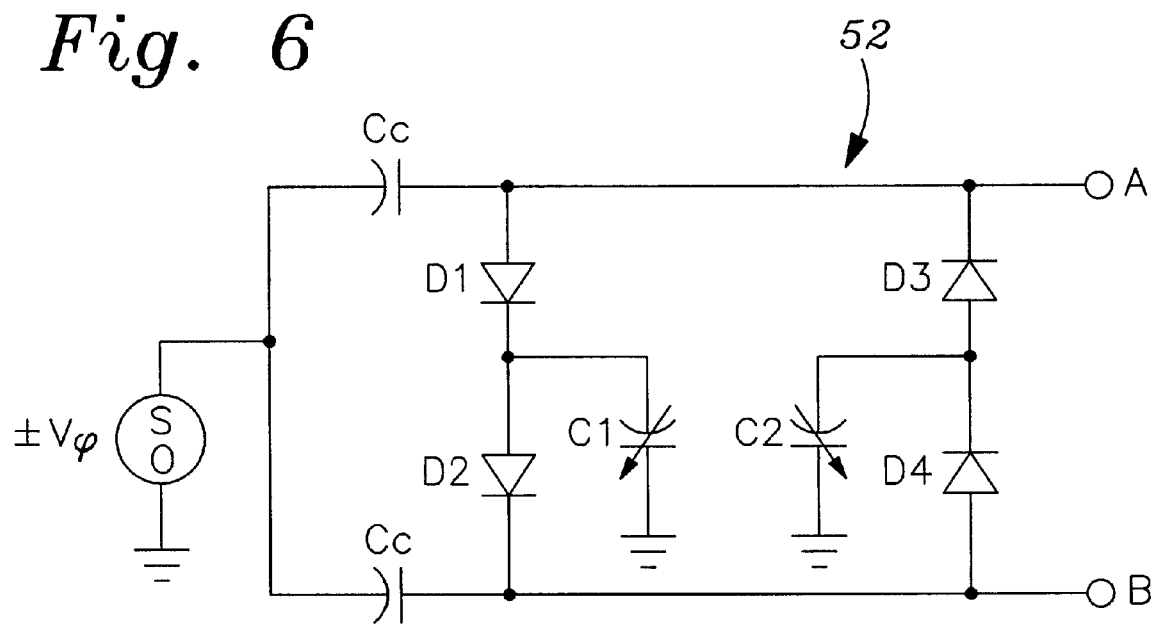
FIG. 6 is an electrical schematic showing the preferred diode quad bridge circuit.

As shown in FIGS. 4–5, the means for measurement is preferably a pressure transducer 40. Pressure transducers are known in the art and those skilled in the field can construct a transducer to the specific needs of the biosensor 10. An example of a transducer is disclosed in Harrison D R, Dimeff J. Rev. Sci. Instrum. 44:1468–1472, (1973) and Harrison et al., U.S. Pat. No. 3,869,676, titled Diode-Quad Bridge Circuit Means, hereby incorporated by reference. In its most preferred embodiment, the means for measuring 40 is a capacitive pressure transducer 40 associated with the flexible diaphragm 28 described above. The preferred transducer 40 includes a first electrode 44 and a second electrode 46, the first and second electrodes 44 and 46 being separated by an insulator 48. In its preferred embodiment, the first and second electrodes 44 and 46, as well as the insulator 48, are coaxially aligned cylinders. The flexible diaphragm 28 is preferably welded to the top of the first conductor 44, converting the diaphragm 28 into one of the electrodes of a capacitor portion of the transducer 40. The first electrode 44 is connected to the diaphragm 28, and the diaphragm 28 is separated from the second electrode 46 by an air gap 50. Since the diaphragm 28 is in mechanical contact with the hydrogel 30, the diaphragm 28 deflects in response to changes in the osmotic pressure of the hydrogel 30, thereby changing the size of the air gap 50 between the second electrode 46 and the diaphragm 28, thereby changing the value of the capacitance. The value of the capacitance change is detected remotely, preferably using a diode quad bridge circuit 52. These pressure transducers 40 have been successfully used to measure pressure changes in flowing polymeric liquids as small as one Pascal.

Examples of alternative transducers are described in Takaki, U.S. Pat. No. 5,711,291 and Fowler, U.S. Pat. No. 5,752,918, hereby incorporated by reference. A more detailed discussion of transducers can be found in the following references, hereby incorporated by reference: Baek S G. Ph.D. Thesis, University of Utah, (1991); Magda J J, Baek S G, Larson R G, DeVries K L. Polymer 32:1794–1797, (1991); Magda J J, Baek S G, Larson R G, DeVries K L. Macromolecules 24:4460–4468, (1991); Magda J J, Lou J, Baek S G. Polymer 32:2000–2009, (1991); Lee C S, Tripp B, Magda J J. Rheologica Acta 31:306–308, (1992); Lee C S, Magda J J, DeVries K L, Mays J W. Macromolecules 25:4744–4750, (1992); Magda J J, Baek S G. Polymer 35:1187–1194, (1994); Lou J. M.S. Thesis, University of Utah, (1992); Fryer T. *Biotelemetry III,* Academic Press, New York, pp.279–282, (1976); Updike S J, Shults M C, Rhodes R K, Gilligan B J, Luebow J O, von Heimburg D. ASAIO J. 40 :157–163, (1994); and Foulds N C, Frew J E, Green M J. Biosensors A Practical Approach (Cass A E G. eds.) IRL Press Oxford University, pp. 116–121, (1990). While a preferred pressure transducer 40 has been described, those skilled in the art can devise other means for measuring 40. One alternative embodiment includes a piezoelectric transducer or sensor. These alternatives are considered equivalent to the described invention.

Means for reporting—Telemeter

Figure 2:
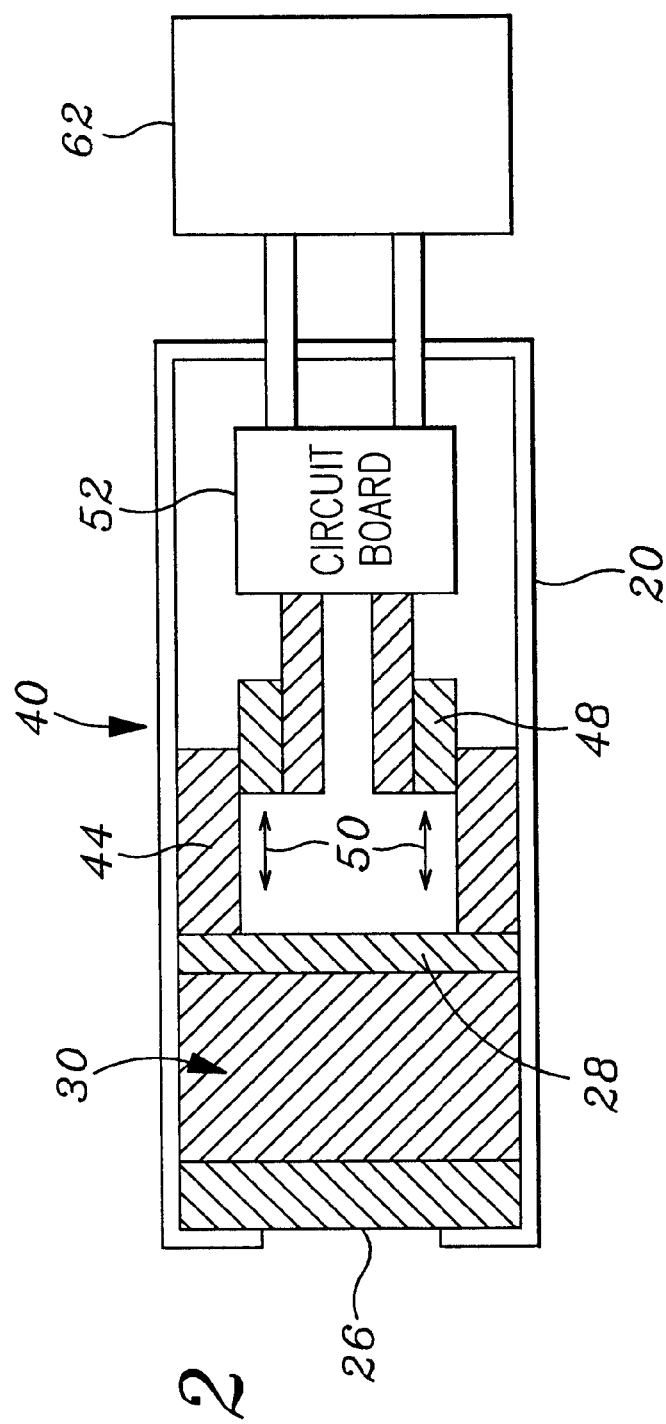
FIG. 2 is a side elevational sectional view of an alternative embodiment thereof, showing a biosensor that is electronically attached to a computer.

Finally, the biosensor 10 includes a means for reporting 60 the concentration of the organic molecule once it has been measured. This element will vary greatly depending upon the specific use of the biosensor 10 as well as the needs of the user. In its simplest form, as shown in FIG. 2, the transducer 40 is simply connected electronically to a computer means, generally a personal computer. The computer compares the data from the transducer 40 to a calibration curve to generate usable data for export through a reporting means. In one embodiment, the computer sounds an alarm if the concentration of the organic molecule exceeds a certain level. in another embodiment, the computer outputs data onto a reporting outlet such as a computer monitor. In yet another embodiment, the computer controls a feedback loop to change a process is response to variation in the concentration of the organic molecule.

In a preferred embodiment, as shown in FIG. 1, the biosensor 10 is a glucose biosensor 10 that can be implanted into the human body. In this case, the means for reporting 60 is preferably a battery powered telemeter 60 that transmits a data signal to a receiver operably connected to the computer. The computer also compares the data signal to a calibration curve and reports the concentration through a reporting means. The reporting means is preferably an audible alarm to warn diabetics if glucose levels get too high or too low. In its most preferred embodiment, the computer also controls an insulin pump to correct the blood glucose level of the diabetic. Ideally, the biosensor 10 would be used on conjunction with an implanted glucose pump and would functionally replace the pancreas in controlling blood glucose levels, allowing diabetics to lead nearly normal lives.

Figure 3:
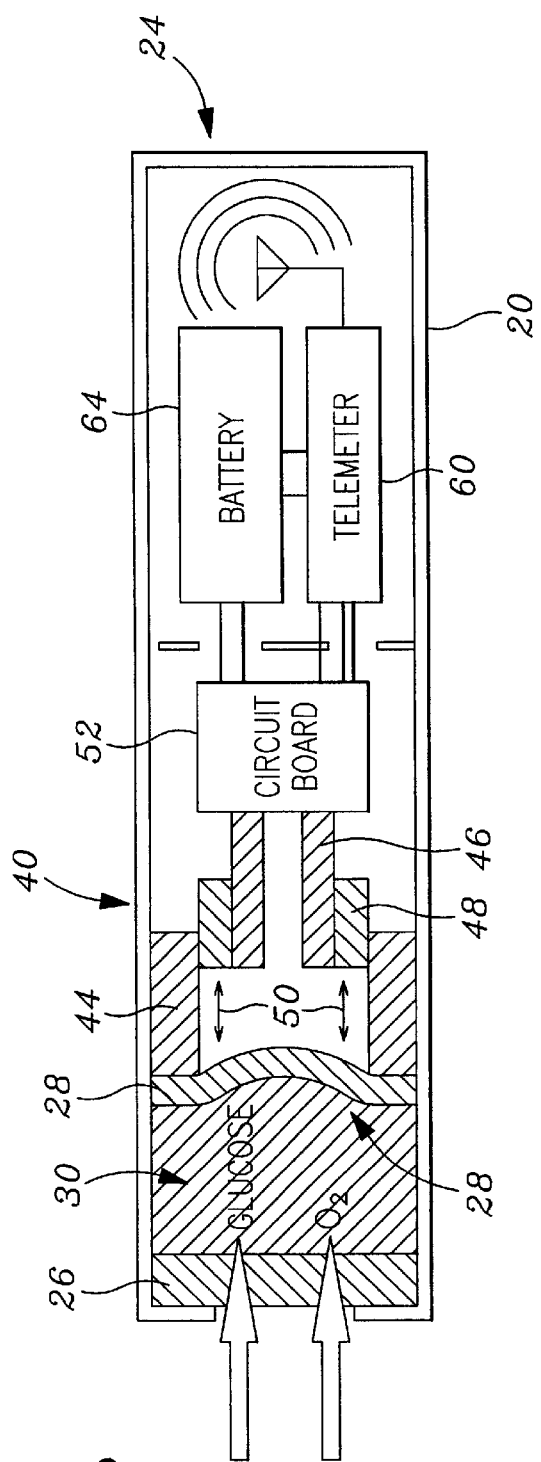
FIG. 3 is a side elevational sectional view of the preferred embodiment, showing glucose and oxygen diffusing into the hydrogel, causing the hydrogel to swell and causing the pressure transducer to signal to a computer through a telemeter.

Method For Using A Biosensor To Measure The Concentration Of An Organic Molecule In A Solution The invention further includes a method for using a biosensor 10 to measure the concentration of an organic molecule in a solution. The method includes the following steps: First, providing a biosensor 10 as described above. An oxidoreductase enzyme is immobilized in the hydrogel 30, preferably using matrix entrapment. The biosensor 10 is preferably first immersed on a buffer and inserted into a control solution. The data generated is then compared to a calibration curve to calibrate the biosensor 10. Once the biosensor 10 is removed and rinsed in another buffer, the biosensor 10 is inserted into the solution. The organic molecules are allowed to diffuse into the polymeric hydrogel 30, causing the oxidoreductase enzyme to catalyze a chemical reaction consuming the organic molecule and producing the byproduct. As described above, the GOD enzyme is preferably used to catalyze a reaction in which oxygen and glucose are transformed into hydrogen peroxide and gluconic acid. The production of gluconic acid causes the pH to lower, thereby causing the hydrogel 30 to increase in osmotic pressure and swell, as shown in FIG. 3. This swelling is measured with the means for measuring 40. The means for measuring 40 is preferably a pressure transducer 40. The pressure transducer 40 is used to measure the osmotic pressure of the hydrogel 30, which is proportional to the pH level in the hydrogel 30 (which is proportional to the concentration of the glucose). Data from the transducer 40 regarding this measurement is then sent to a means for reporting 60. In an implantable biosensor 10, a battery powered telemeter 60 is used to transmit the data to a computer. This can be then reported to the user through a computer monitor, an audible alarm, or a feedback system such as an automatic insulin pump (as described above). Throughout use, the system can be recalibrated by taking blood samples and comparing the glucose readings to those reported by the biosensor 10. The computer actuated means of calibration can then be adjusted to correct for any errors.

In addition to the above-described disclosure, it is useful to consider the detailed disclosures made in the following references, hereby incorporated by reference: Wilkins E, Atanasov P, and Muggenburg B A. Biosens. Bioelectron.

10:485–494, (1995); Aussedat B, Thome-Duret V., Reach G., Lemmonier F., Klein J C, Hu Y., and Wilson G S. Biosens. Bioelectron. 12:1061–1071, (1997); von Woedtke T, Fischer U., Brunstein E, Rebrin K, and Abel P. J. Artif. Organs 14:473–481, (1991); Fisher U. Acta Anaesthesiol Scand Suppl. 104:21–29, (1995); Wilkins E, and Atanasov P. Med.Eng.Phys. 18:273–288, (1996); Luong J H T, Mulchandani A, and Guilbault G. Tibtech 6:310–316, (1988); Fischer U. Diabetic Med. 8:309–321, (1991); Pickup J C. Lancet 2:817–820, (1985); Mercado R C, Moussy F. Biosens Bioelectron. 13:133–145, (1998); Yang Q, Atanasov P, Wilkins E. Biomed Instrum Technol. 31:54–62, (1997); Yang S, Atanasov P, Wilkins E. Biomed Instrum Technol. 30:55–61, (1996); Ohashi E, Karube I J Biotechnol. 40:13–19, (1995); Yang S, Atanasov P, Wilkins E. Biomed Instrum Technol 29:125–133, (1995); Wilkins E, Atnnasov P, Muggenburg B A Biosens Bioelectron. 10:485–494, (1995); Linke B, Kemer W, Kiwit M, Pishko M, Heller A. Biosens. Bioelectron. 9:151–158, (1994); Pickup J C, Claremont D J. Horm Metab Res Suppl. 20: 34–36, (1988); Abel P, Fischer U, Brunstein E, Ertle R Horm Metab Res Suppl. 20:26–29, (1988); Cass A E G, Davis G, Francis C D, Hill H A O, Aston W J, Higgins T J, Plotkin E V, Scott L D, Turner A P F. Anal. Chem. 56:667–71, (1984); Clark L C, Lyons C. Ann, NY Acad. Sci. 102:29–45, (1962); Updike S J, Hicks G P. Nature 214:986–988, (1967); Albery W J, Bartlett P N, Boutelle M G, Fillenz M. J. Physiol. 382:93–97, (1986); Xie S L, Wilkins E. Atanasov P. Sensors & Actuators 17:133–142, (1993); Atanasov P, Kaisheva A. Iliev I, Razumas V, Kulys J. Biosens Bioelectron. 7:361–365, (1992); Reddy S M, Vadgama. Handbook of biosensors and electronic noses: medicine, food, and the environment (Kress-Rogers E, eds.) CRC Press, pp. 111–135, (1997); Kell D B, Davey C L. Biosensors, A practical approach. (Cass A E G eds.) Oxford University Press, Oxford, pp.125–155, (1990); Bergveld P. IEEE Trans Biomed Eng 17:70–71, (1970); Meyerhoff C, Mennel F J, Sternberg F, Pfeiffer E F. The Endocrinologist 6:51–58, (1990); Armour J C, Lucisano J Y, McKean B D, Gough D A. Diabetes 39:1519–1526, (1990); Atanasov P. Wilkins E. Anal. Lett. 28:1587–1612, (1993); Klumb L A, Horbett T A. J. Control. Release 18:59–80, (1992); Claremont D J, Sambrook I E, Penton C, Pickup J C. Diabetologia 29:817–821, (1986); Ishihara K, Kobayashi M, Shionohara I. Makromol. Chem. Rapid Commun. 4:327–331, (1983); Sato S, Jeong S Y, McRea J C, Kim S W. J. Control. Release 1:67–77, (1984); Ito Y, Casolaro M, Kono K, Imanishi Y. J. Control. Release 10:195–203,(1989) ;Gehrke S H. Adv.PolymerSci. 110:83–144,(1993); Pedley D G, Skelly P J, Tighe B J. Br. Polym. J. 12:99–100, (1980) Brondsted H, Kopecek J. Polyelectrolyte gels: Properties, Preparation, and Application (Harland R S, Prud homme P K. eds.) pp. 285–304, (1992); Feil H, Bae Y H, Feijen J, Kim S W. Macromolecules 25:5528–5530, (1992); Kim S W, Bae Y H, Okano T. Pharm Res. 9:283–290, (1992); Kim Y H, Bae Y H, Kim S W. J. Control Release 28:143–152, (1994); Bell C L, Peppas N A. Biomaterials 17:1203–1218, (1996); De Moor C P, Doh L, Siegel, R A. Biomaterials 12:836–840 , (1991); Siegel R A, Firestone B A. Macromolecule 21:3254–3259, (1988); Batich C D, Yan J, Bucaria Jr. C, Elsabee M. Macromolecules 26:4675–4680, (1993) Vakkalanka S K. Brazel C S, Peppas N A. J. Biomater. Sci. Polym. Ed. 8:119–129, (1996); Ghandehari H, Kopeckovd P, Yeh P-Y, Kopecek J. Macromol. Chem. Phys. 197:965–980, (1996); gayn V, Walt D R. ACS symposium series 556 Diagnostic Biosensor polymers (Usmani A M,Akmal N. eds.) American Chemical Society, Washington pp. 21–33, (1994); Khare A R, Peppas N A. Biomaterials 16:559–567, (1995); Allcock H R, Ambrosio A M. Biomaterials 17:2295–2302, (1996); Siegel R A, Johannes I, Hunt C A, Firestone B A. Pharm Res 9:76–81, (1992); Vazquez B, Gurruchaga M, San Roman J. Biomaterials 18:521–526, (1997); Brannon-Peppas L, Peppas N A. Biomaterials 11:635–644, (1990); Ofrier C M, Schott H. J. Pharm Sci 75:790–796, (1986); Ishihara K. Kobayashi M. Ishimaru N. Shinohara I. Poly J. 16:625–631, (1984); Serres A, Baudys M, Kim S W. Pharm Res. 13:196–201, (1996); agasaki Y, Honzawa E, Kato M, Kataoka K, Tsuruta T. Macromolecules 27:4848–4850,(1994); Kuhn W, Hargitay B.

Nature 165:514–516, (1950); eymour R B, Carraher Jr C E. Polymer Chemistry: An Introduction (Hiemenz PC. 3rd eds.),Marcel Dekker, Inc., New York, pp 1–752, (1992); Wichterle 0. In Encyl. Polym. Sci. and Technol. (Gaylord N G eds.) 15:273–291, (1971); Voldrich Z, Tomanek Z, Vacik J, Kopecek J. S. Biomed. Mater. Res. 9:675–685, (1975); Arica Y, Hasirci V N. Biomaterials 8:489–495, (1987); Firestone B A, Siegel R A. J. Biomater Sci. Polym. Ed. 5:433–450, (1994); Kou J H. Amidon G L, Lee P I. Pharm. Res. 5:592–597, (1988); Quinn C P, Pathak C P, Heller A, Hubbell J A. Biomaterial 16:389–396, (1995); Gursel 1, Hasirci V N.

Biomaterials 13:150–150, (1992); Doretti L, Ferrara D. Biosens. Bioelecton. 11:365–373, (1996); Arica M Y, Hasirci V. Biomaterials 14:803–808, (1993); Constantinides A, Vieth W R, Fernandes P M. Mol Cell Biochem. 11:127–133, (1973); Schlosser M, Ziegler B, Abel P, Fischer U, Ziegler. Horm. Metab. Res. 26:534–537, (1994); and Puers P. Sensors and Actuators A, vol. 37:93–105, (1993).

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A biosensor 10 for measuring the concentration of an organic molecule, the biosensor comprising:
   a polymeric hydrogel that changes its osmotic pressure in proportion to the concentration of a byproduct;
   an oxidoreductase enzyme immobilized in the hydrogel, the oxidoreductase enzyme catalyzing a chemical reaction consuming the organic molecule and producing the byproduct, thereby causing the hydrogel to change its osmotic pressure;
   a means for measuring the osmotic pressure of the hydrogel; and a means for reporting the concentration of the organic molecule based on the measured osmotic pressure of the hydrogel.

2. The biosensor of claim 1 further comprising an enclosure containing the hydrogel, the enclosure having an open end sealed by a semipermeable membrane that allows oxygen and the organic molecule to diffuse into the hydrogel.

3. The biosensor of claim 2 wherein the enclosure further includes a flexible diaphragm, the hydrogel being enclosed between the flexible diaphragm and the semipermeable membrane, the flexible diaphragm working in conjunction with the means for measuring to monitor changes in the osmotic pressure of the hydrogel.

4. The biosensor of claim 3 wherein the enclosure is conjugated with heparin and polyethylene glycol.

5. The biosensor of claim 1 wherein the hydrogel includes crosslinking that allows oxygen to diffuse into the hydrogel at a greater rate than the organic molecule.

6. The biosensor of claim 1 wherein the hydrogel includes pendant groups having a pKa value between 11 and 3.

7. The biosensor of claim 1 wherein the hydrogel includes nicotinamide moieties.

8. The biosensor of claim 1 wherein the hydrogel is biocompatible, nontoxic, and inert in the body.

9. The biosensor of claim 1 wherein the oxidoreductase enzyme is glucose oxidase.

10. The biosensor of claim 1 further including a catalase immobilized in the hydrogel.

11. The biosensor of claim 1 wherein the means for measuring is a pressure transducer.

12. The biosensor of claim 1 wherein the means for measuring is a piezoelectric transducer.

13. The biosensor of claim 1 wherein the means for reporting is a battery powered telemeter that transmits a data signal to a receiver operably connected to a computer means, the computer means comparing the data signal to a calibration curve to calculate the concentration of the organic molecule, the computer means then reporting the concentration through a reporting means.

14. The biosensor of claim 10 wherein the means for reporting is a computer electrically connected to the means for measuring, the computer comparing data from the means for measuring to a calibration curve to calculate the concentration of the organic molecule, the computer means then reporting the concentration through a reporting means.

15. The biosensor of claim 14 wherein the hydrogel further includes an oxygen substitute.

16. The biosensor of claim 1 further including an oxygen reservoir operably connected to the hydrogel to provide an increased supply of oxygen to the oxidoreductase enzyme.

17. A biosensor for measuring the concentration of glucose in a person, the biosensor comprising:

a rigid, biocompatible enclosure having an open end and a closed end, the open end being covered by a semipermeable membrane; a flexible diaphragm being positioned between the semipermeable membrane and the closed end; and a polymeric hydrogel enclosed between the semipermeable membrane and the diaphragm, the hydrogel including moieties that cause the hydrogel to change its osmotic pressure in proportion to the pH of the hydrogel;

an amount of glucose oxidase immobilized in the hydrogel;

a capacitance pressure transducer operatively engaged to the diaphragm; and a battery powered telemeter operatively engaged to the transducer.

18. The biosensor of claim 17 further including a catalase immobilized in the hydrogel.

19. A method for using a biosensor to measure the concentration of an organic molecule in a solution, the method comprising the steps of:

a) providing a biosensor comprising:

a rigid, biocompatible enclosure having an open end and a closed end, the open end being covered by a semipermeable membrane; a flexible diaphragm being positioned between the semipermeable membrane and the closed end; and a polymeric hydrogel enclosed between the semipermeable membrane and the diaphragm, the hydrogel including moieties that cause the hydrogel to change its osmotic pressure in proportion to the pH of the hydrogel;

an oxidoreductase enzyme immobilized in the hydrogel a means for measuring the osmotic pressure of the hydrogel, the means for measuring being associated with the diaphragm; and a means for reporting the concentration of the organic molecule based on the measured osmotic pressure of the hydrogel;

b) providing a solution, the solution containing an amount of the organic molecule;

c) inserting the biosensor into the solution;

d) allowing the organic molecule to diffuse into the polymeric hydrogel;

e) allowing the oxidoreductase enzyme to catalyze a chemical reaction consuming the organic molecule and producing the byproduct;

f) measuring the osmotic pressure of the hydrogel with the means for measuring;

g) sending data regarding the osmotic pressure of the hydrogel from the means for measuring to the means for reporting; and h) reporting the concentration of the organic molecule based upon the osmotic pressure of the hydrogel measured by the means for measuring.

20. The method of claim 19 further comprising the step of:

a') inserting the biosensor into a buffer.

a") inserting the biosensor into a control solution and comparing the data generated to a control curve, thereby calibrating the biosensor ; and a'") rinsing the biosensor in the buffer.

* * * * *